(12) United States Patent
Tan et al.

(10) Patent No.: US 9,370,764 B2
(45) Date of Patent: *Jun. 21, 2016

(54) COMPOSITIONS AND PARTICLES CONTAINING CELLULOSIC FIBERS AND STABILIZED-AND/OR ACTIVATED-UREASE INHIBITORS, AS WELL AS METHODS OF MAKING AND USING THE SAME

(71) Applicant: INTERNATIONAL PAPER COMPANY, Memphis, TN (US)

(72) Inventors: Zheng Tan, Princeton, NJ (US); Gopal C. Goyal, Mason, OH (US); Linnea J. Shaver, Maineville, OH (US)

(73) Assignee: International Paper Company, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,434

(22) Filed: Jul. 22, 2014

(65) Prior Publication Data

US 2014/0349835 A1    Nov. 27, 2014

Related U.S. Application Data

(63) Continuation of application No. 12/154,653, filed on May 23, 2008, now Pat. No. 8,809,616.

(60) Provisional application No. 60/931,682, filed on May 23, 2007.

(51) Int. Cl.
| | | |
|---|---|---|
| *B01J 20/24* | (2006.01) | |
| *A61K 47/38* | (2006.01) | |
| *D21C 9/00* | (2006.01) | |

(52) U.S. Cl.
CPC .............. *B01J 20/24* (2013.01); *A61K 47/38* (2013.01); *D21C 9/00* (2013.01); *B01J 2220/44* (2013.01)

(58) Field of Classification Search
None
See application file for complete search history.

(56) References Cited

U.S. PATENT DOCUMENTS

| | | | | |
|---|---|---|---|---|
| 3,843,701 | A | * | 10/1974 | Wortham ...................... 556/182 |
| 3,849,701 | A | * | 11/1974 | Kerfoot et al. ................ 315/101 |
| 4,022,965 | A | | 5/1977 | Goheen et al. |
| 4,075,136 | A | | 2/1978 | Schaper |
| 4,166,894 | A | | 9/1979 | Schaper |
| 4,174,417 | A | | 11/1979 | Rydell |
| 4,431,481 | A | | 2/1984 | Drach et al. |
| 4,496,427 | A | | 1/1985 | Davison |
| 4,539,037 | A | | 9/1985 | Seredloff et al. |

(Continued)

FOREIGN PATENT DOCUMENTS

| | | |
|---|---|---|
| EP | 0356677 | 7/1989 |
| EP | 0389023 | 3/1990 |

(Continued)

OTHER PUBLICATIONS

Alfred Burger, Isosterism and Bioisosterism in Drug Design, in Progress in Drug Research 287-328 (Ernst Jucker, ed., Birkhauser Verlag, 1991).

(Continued)

*Primary Examiner* — Ernst V Arnold
*Assistant Examiner* — Jianfeng Song
(74) *Attorney, Agent, or Firm* — Thomas W. Barnes, III (57) ABSTRACT

The present invention relates to compositions containing stabilized and/or activated urease inhibitors, as well methods of making and using the same.

31 Claims, 6 Drawing Sheets

(56) References Cited

U.S. PATENT DOCUMENTS

| | | | |
|---|---|---|---|
| 4,986,882 | A | 1/1991 | Mackey et al. |
| 5,049,235 | A | 9/1991 | Barcus et al. |
| 5,160,789 | A | 11/1992 | Barcus et al. |
| 5,209,953 | A | 5/1993 | Grupe et al. |
| 5,266,250 | A | 11/1993 | Kroyer |
| 5,360,420 | A | 11/1994 | Cook et al. |
| 5,443,899 | A | 8/1995 | Barcus et al. |
| 5,531,728 | A | 7/1996 | Lash |
| 5,662,773 | A | 9/1997 | Frederick et al. |
| 5,667,637 | A | 9/1997 | Jewell et al. |
| 5,698,074 | A | 12/1997 | Barcus et al. |
| 5,698,688 | A | 12/1997 | Smith et al. |
| H1704 | H | 1/1998 | Wallajapet et al. |
| 5,731,080 | A | 3/1998 | Cousin et al. |
| 6,146,494 | A | 11/2000 | Seger et al. |
| 6,229,062 | B1 | 5/2001 | Mandell et al. |
| 6,287,550 | B1 * | 9/2001 | Trinh et al. ................ 424/76.6 |
| 6,342,653 | B1 | 1/2002 | Gancet et al. |
| 6,361,651 | B1 | 3/2002 | Sun |
| 6,471,824 | B1 | 10/2002 | Jewell |
| 6,506,282 | B2 | 1/2003 | Hu et al. |
| 6,579,414 | B2 | 6/2003 | Jewell |
| 6,579,415 | B2 | 6/2003 | Jewell |
| 6,582,557 | B2 | 6/2003 | Jewell |
| 6,592,712 | B2 | 7/2003 | Koukoulas et al. |
| 6,592,717 | B2 | 7/2003 | Jewell |
| 6,828,014 | B2 | 12/2004 | Branham et al. |
| 6,893,473 | B2 | 5/2005 | Neogi et al. |
| 2003/0024661 | A1 | 2/2003 | Shore et al. |
| 2004/0112297 | A1 | 6/2004 | Rasner et al. |
| 2006/0029567 | A1 | 2/2006 | Dutkiewicz |
| 2006/0185808 | A1 | 8/2006 | Nguyen |
| 2006/0260773 | A1 | 11/2006 | Tan et al. |
| 2007/0051481 | A1 | 3/2007 | Tan et al. |
| 2007/0077428 | A1 * | 4/2007 | Hamed et al. ................ 428/393 |
| 2007/0119556 | A1 | 5/2007 | Tan et al. |
| 2007/0193707 | A1 | 8/2007 | Mguyen |
| 2007/0277947 | A1 | 12/2007 | Nguyen |
| 2008/0066878 | A1 | 3/2008 | Nguyen |

FOREIGN PATENT DOCUMENTS

| | | | |
|---|---|---|---|
| EP | 0408199 | | 6/1990 |
| WO | 9422500 | | 10/1994 |
| WO | 9628431 | | 9/1996 |
| WO | 9826808 | | 6/1998 |
| WO | WO98-26808 | * | 6/1998 |
| WO | 2007041039 | | 4/2007 |
| WO | 2008153753 | | 12/2008 |

OTHER PUBLICATIONS

Oxford English Dictionary: "Inert," available at www.oed.com, retrieved on Jul. 27, 2011.

Ivan Rossi et al., Modeling Hindered-Amine Light Stabilizer-Promoted Polymer Stabilization: Computational Insight Into the Mechanism for Nitroxyl Radical Regeneration from Aminoethers, 121 J Am. Chem. Soc. 7914 (1999).

Investigation of hydroxamic acids as laccase-mediators for pulp bleaching, X. Geng, K. Li, F.Xu, Appl Microbial Biotechnol (2004) 64:p. 493-496.

* cited by examiner

COMPOSITIONS AND PARTICLES CONTAINING CELLULOSIC FIBERS AND STABILIZED-AND/OR ACTIVATED-UREASE INHIBITORS, AS WELL AS METHODS OF MAKING AND USING THE SAME

The present application claims the benefit of priority under 35 USC §119(e) to U.S. Provisional Patent Application 60/931,682, filed May 23, 2007, which is hereby incorporated, in its entirety, herein by reference.

FIELD OF THE INVENTION

The present invention relates to compositions containing stabilized and/or activated urease inhibitors, as well as methods of making and using the same.

DETAILED DESCRIPTION OF THE INVENTION

The inventors have found compositions containing cellulosic fibers and stabilized- and/or activated-urease inhibitors.

The composition of the present invention may contain at least one urease inhibitor. The urease inhibitor may be any chemical or mixtures of chemicals that are capable of inhibiting, preventing, and/or reducing the tendency of a urease protein to degrade urea. Ureases are well known proteins produced by microorganisms to break down and/or degrade urea and/or modified ureas. Examples of ureases, the microorganisms that produce ureases, as well as urease inhibitors can be found in "Improving Efficiency of Urea Fertilizers by Inhibition of Soil Urease Activity" by S. Kiss and M. Simihaian which was published in 2002 by Kluwer Academic Publishers, but are not limited to those described in this reference. Further examples of urease inhibitors can be found in U.S. Pat. Nos. 4,539,037 and 6,828,014; PCT Published Patent Application WO 98/26808; United States Patent Application Publications 2006/0029567 and 2007/0077428, which are all hereby incorporated, in their entirety, herein by reference.

Further examples of urease inhibitors include organic and inorganic compounds. Examples of inorganic compounds include boron compounds, fluorides, and sulfur compounds. Examples of organic compounds include, organo boron acid compounds, hexamethylenetetamine, urea derivatives, dithiocarbamates, thiuram disulfides, sulfides, xanthates, hydroxamic acids such as the mono and di-hydroxamic acids, maleimides, maleic hydrazide, mucochloric acid, bromo-nitro compounds, heterocyclic sulfur compounds, phosphorus containing compounds and phosphohorothioate containing compounds, phosphoromonoamidates, phosphorodiamidates, thiophosphorodiamidates, phenylphosphorodiamidate (PPDA), polyphosphomdiamides, phosphorodiamidic acid esters, diamidophosphorothiolates, diamidothiophosphorothiolates, phosphoric triamides, thiophosphoric triamides, N-alkylated phosphoric triamide, cyclohexyl phosphoric triamide, N-butyl phosphoric triamide, N-butyl thiophosphoric triamide, and any mixture thereof.

By "alkylated" used above the urease inhibitor contains an alkyl group. The alkyl group may be of any number of carbon atoms and may be further modified by an amine, hydroxyl, ester, ether, and/or carboxyl/carbonyl functionality. Preferably, the alkyl group is not modified and contains from 1 to 12 carbon atoms, more preferably from 1 to 6 carbon atoms. Further, the alkyl group may be a methyl, ethyl, N-propyl, isopropyl, N-butyl, iso-butyl, tert-butyl, pentyl, cyclopentyl, hexyl, and cyclohexyl group. Accordingly, the alkyl group may be cyclic and/or may be aromatic.

Preferred phosphorodiamidates include phenylphosphorodiamidate (PPDA). Preferred N-alkylated phosphoric triamides include cyclohexyl phosphoric triamide and N-butyl phosphoric triamide. Preferred N-alkylated thiophosphoric triamides include N-butyl thiophosphoric triamide (NBTP).

The composition may contain the at least one urease inhibitor at any amount, including from 0.05 ppm to 10 wt %, preferably from 1 ppm to 2 wt %, more preferably from 5 ppm to 5,000 ppm, most preferably from 10 to 1500 ppm of the at least one urease inhibitor based upon the total weight of the composition.

The composition of the present invention may contain at least one stabilizer. In this sense the stabilizer preferably stabilizes the urease inhibitor when present in the composition. Examples of stabilizers include, but are not limited to alkylene oxides such as those having from 2 to 6 carbon atoms, polyalkylene oxides such as those having from 2 to 6 carbon atoms, polyethylene oxides, ethylene oxides, propylene oxides, polypropylene oxides, diethylene oxides, dipropylene oxides, glycerin, diypropylene glycol, ethylene glycol, polypropylene glycol, substituted ethylene glycols such as methoxyethylene glycols, ethylene glycol ethers such as ethylene glycol monobutyl ether and ethylene glycol monoethyl ether.

The stabilizer may have any melting temperature ($T_m$). In one embodiment the stabilizer may be a liquid at room temperature and have a melting temperature that is not more than room temperature. In another embodiment, the stabilizer may be in the form of a solid at room temperature and have a melting temperature that is at least room temperature, preferably from room temperature to 125° C., more preferably at least 60° C.

The composition may contain the at least one stabilizer at any amount, including from 0.1 to 99.99 wt % based upon the total weight of the composition, preferably from 0.1 to 10 wt % based upon the total weight of the composition, more preferably from 0.1 to 5 wt % based upon the total weight of the composition.

The composition may contain at least one activator. The activator may include hindered amines such as those having the following chemical formula:

where $R_0$ is a —O radical, —OH, —O-phenyl, —O-alkyl preferably substituted or unsubstituted having from 1 to 6 carbon atoms, and —H; where $R_1$ is hydrogen, oxo, hydroxy, acetoamido, or phosphonooxy groups. The activators may be 2,2,6,6-tetramethyl piperidine and derivatives thereof, 2,2,6,6-Tetramethylpiperidine-1-oxyl (TEMPO), 4-hydroxy-2,2,6,6-Tetramethylpiperidine-1-oxyl (4-hydroxy TEMPO), 4-oxy-TEMPO, 4-acetamido-TEMPO, 4-phosphonooxy-TEMPO, N-hydroxybenzotriazole, N-hydroxymaleimide, N-hydroxysuccinamide, N-hydroxyphthalimide, hydroxybenzothiazole, oxa-benzotrazole, d- and aza-pyridine-triazole, violuric acid, and UV absorbers based on benzotriazole, as well as mixtures thereof. Further, any one of these activators may be used in combination with any oxidant and/or oxidative enzyme. Examples of oxidants are perborates and percarbonates. An example of an oxidative enzyme is lacasse (examples of reductases).

The composition may contain the at least one activator at any amount, including from 1 ppm to 10 wt %, preferably from 100 ppm to 10%, more preferably from 0.1 wt % to 10 wt %, based upon the total weight of the composition.

The composition of the present invention may also contain at least one inert substance. Examples of inert substances may include, but is not limited to, desiccants, talc, talc powder, stearates, calcium stearate, stearic acid, palmitates, zeolites, calcium chloride, calcium carbonate, ammonium chloride, anhydrous silica, calcium silicates, aluminosilicates such as Hydrex, diatomaceous earth, phosphates, sodium phosphate, potassium phosphates, ammonium phosphates, calcium phosphates, hydroxyapatite, superabsorbent polymers, polyvinyl polypyrrolidone (PVPP), alumina, silica, and mixtures thereof. Preferable inert substances include those having moisture barrier forming compounds and moisture absorbing compound. Examples of moisture absorbing compounds are desiccants.

If the inert particle is a superabsorbent particle, the superabsorbent particle may be of any size and shape such as a powder, a fiber, or a disk. In one embodiment, the superabsorbent particle may be not greater than 1000 microns, preferably not greater than a 100 microns.

The composition may contain the at least one inert substance at any amount, including from 0.1 to 10 wt % based upon the total weight of the composition.

The composition of the present invention may also contain at least one preservative. Examples of the preservative include, but is not limited to, parabens, polyparaben, benzoates, benzoate esters, phenolsulfonic acids, and mixtures thereof.

The composition of the present invention may contain at least one cellulosic fiber. Examples of the cellulosic fiber include fiber derived from hardwood trees, softwood trees, or a combination of hardwood and softwood trees prepared for use in a papermaking furnish and/or fluff pulp furnish by any known suitable digestion, refining, and bleaching operations. The cellulosic fibers may be recycled fibers and/or virgin fibers. Recycled fibers differ from virgin fibers in that the fibers have gone through the drying process at least once. In certain embodiments, at least a portion of the cellulose/pulp fibers may be provided from non-woody herbaceous plants including, but not limited to, kenaf, hemp, jute, flax, sisal, or abaca although legal restrictions and other considerations may make the utilization of hemp and other fiber sources impractical or impossible. Either bleached or unbleached pulp fiber may be utilized in the process of this invention. High yield pulps and/or mechanical pulps such as TMP, CMP, and BCTMP are also included as the cellulosic fiber of the present invention.

Preferably, the sources of the cellulose fibers are from softwood and/or hardwood species. In one embodiment the source is softwood. In another embodiment, the source is at least 50 wt %, sometimes at least 95 wt %, softwood based upon the total weight of the fibers.

The composition of the present invention may contain the cellulosic fiber at any amount, including at least 60 wt % cellulosic fibers, preferably at least 70 wt %, more preferably at least 80 wt %, most preferably at least 90 wt %, based upon the total weight of the composition.

Further, the cellulosic fibers, preferably softwood and/or hardwood cellulosic fibers, contained by the composition of the present invention may be modified by physical and/or chemical means. Examples of physical means include, but is not limited to, electromagnetic and mechanical means. Means for electrical modification include, but are not limited to, means involving contacting the fibers with an electromagnetic energy source such as light and/or electrical current. Means for mechanical modification include, but are not limited to, means involving contacting an inanimate object with the fibers. Examples of such inanimate objects include those with sharp and/or dull edges. Such means also involve, for example, cutting, kneading, pounding, impaling, etc means.

Examples of chemical means include, but, is not limited to, conventional chemical fiber modification means including crosslinking and precipitation of complexes thereon. Examples of such modification of fibers may be, but is not limited to, those found in the following U.S. Pat. Nos. 6,893,473; 6,592,717, 6,592,712, 6,582,557, 6,579,415, 6,579,414, 6,506,282, 6,471,824, 6,361,651, 6,146,494, H1,704, 5,731,080, 5,698,688, 5,698,074, 5,667,637, 5,662,773, 5,531,728, 5,443,899, 5,360,420, 5,266,250, 5,209,953, 5,160,789, 5,049,235, 4,986,882, 4,496,427, 4,431,481, 4,174,417, 4,166,894, 4,075,136, and 4,022,965, which are hereby incorporated, in their entirety, herein by reference. Further modification of fibers is found in United States Patent Publication Numbers 20060185808; 20060260773; 20070051481; 20070119556; 20070193707; 20070277947; and 20080066878 which are hereby incorporated, in their entirety, herein by reference.

The cellulosic fiber may also be in the form of fines. Sources of "Fines" may be found in SaveAll fibers, recirculated streams, reject streams, waste fiber streams. The amount of "fines" present in the composition can be modified by tailoring the rate at which such streams are added to the papermaking process and/or fluff pulp making process.

In one embodiment, any of the above-mentioned fibers may be treated so as to have a high ISO brightness. Examples of such fibers treated in this manner include, but is not limited to, those described in United States Patent Publication Number 2006-0185808; U.S. patent application Ser. No. 11/445,809 entitled "Pulp and Paper Having Increased Brightness" filed Jun. 2, 2006; and U.S. patent application Ser. No. 11/446,421 entitled "IMPROVED PROCESS FOR MANUFACTURING PULP, PAPER AND PAPERBOARD PRODUCTS" filed Jun. 2, 2006; which are hereby incorporated, in their entirety, herein by reference. The fiber may have any brightness, including at least 80, at least 85, at least 90, and at least 95 Iso Brightness.

The cellulosic fiber may have any brightness and/or CIE whiteness. Examples of measuring CIE whiteness and obtaining such whiteness in a fiber and paper made therefrom can be found, for example, in U.S. Pat. No. 6,893,473, which is hereby incorporated, in its entirety, herein by reference.

The composition may or may not contain water. In one embodiment, the composition may contain at least one cellulosic fiber, at least one urease inhibitor, at least one stabilizer and preferably substantially no water. In another embodiment, the composition may contain at least one cellulosic fiber, at least one urease inhibitor, at least one activator, and optionally water.

In one embodiment of the present invention, the composition may contain at least one cellulosic fiber, at least one urease inhibitor, and at least one polymer having a melting temperature of from room temperature to 125° C. Preferably, the polymer is also a stabilizer as discussed above. The composition may or may not contain water, but preferably contains substantially no water. The composition may contain a superabsorbent particle. When the composition contains a superabsorbent particle, the superabsorbent particle may have any particle size. Preferably, the particle size of the superabsorbent particle is not more than 100 microns. Preferably, the composition itself is in the form of a particle. More preferably, the polymer provides a coating on the at least one cellulosic fiber. Even more preferably, the urease inhibitor and optionally the superabsorbent particle are present in the polymeric coating of the at least one cellulosic fiber.

In one particular embodiment, when at least one urease inhibitor and at least one cellulosic fiber is present in the composition of the present invention, it is preferred that from 0.5 ppm to 10 wt % of the urease inhibitor is present based upon the total amount of the cellulosic fiber. When at least one stabilizer, at least one urease inhibitor, and at least one cellulosic fiber is present in the composition of the present invention, it is preferred that from 0.1 to 20 wt % of the stabilizer is present based upon the total amount of the cellulosic fiber. When at least one activator, at least one urease inhibitor, and at least one cellulosic fiber is present in the composition of the present invention, it is preferred that from 1 ppm to 10 wt % of the activator is present based upon the total amount of the cellulosic fiber. When at least one inert substance, at least one urease inhibitor, at least one cellulosic fiber and optionally at least one stabilizer and/or optionally at least one activator are present in the composition of the present invention, it is preferred that from 0.1 to 10 wt % of the inert substance is present based upon the total weight of the composition.

The composition of the present invention may also contain optional compounds such as optical brightening agents, whiteners, biocides, enzymes, and starch.

The composition of the present invention may be made by any conventional manner of contacting or mixing at least one urease inhibitor with at least one stabilizer and/or at least one activator mentioned above; optionally at least one inert substance, and optionally at least one cellulosic fiber. The at least one urease inhibitor may be serially, consecutively, and/or simultaneously contacted with at least one stabilizer and/or at least one activator mentioned above; optionally at least one inert substance, and optionally at least one cellulosic fiber.

The above contacting may occur at any temperature. In one embodiment, the contacting is performed at a temperature that is greater than the melting, temperature of the stabilizer such that at least the urease inhibitor is dissolved in the stabilizer. Subsequently, the resultant composition may be cooled, preferably to room temperature.

In one embodiment, the a composition containing the urease inhibitor and the stabilizer is contacted with at least one surface of a web of fiber. The composition may be applied to the entire surface of at least one side of the web of just a fraction or portion thereof.

Figure 1:
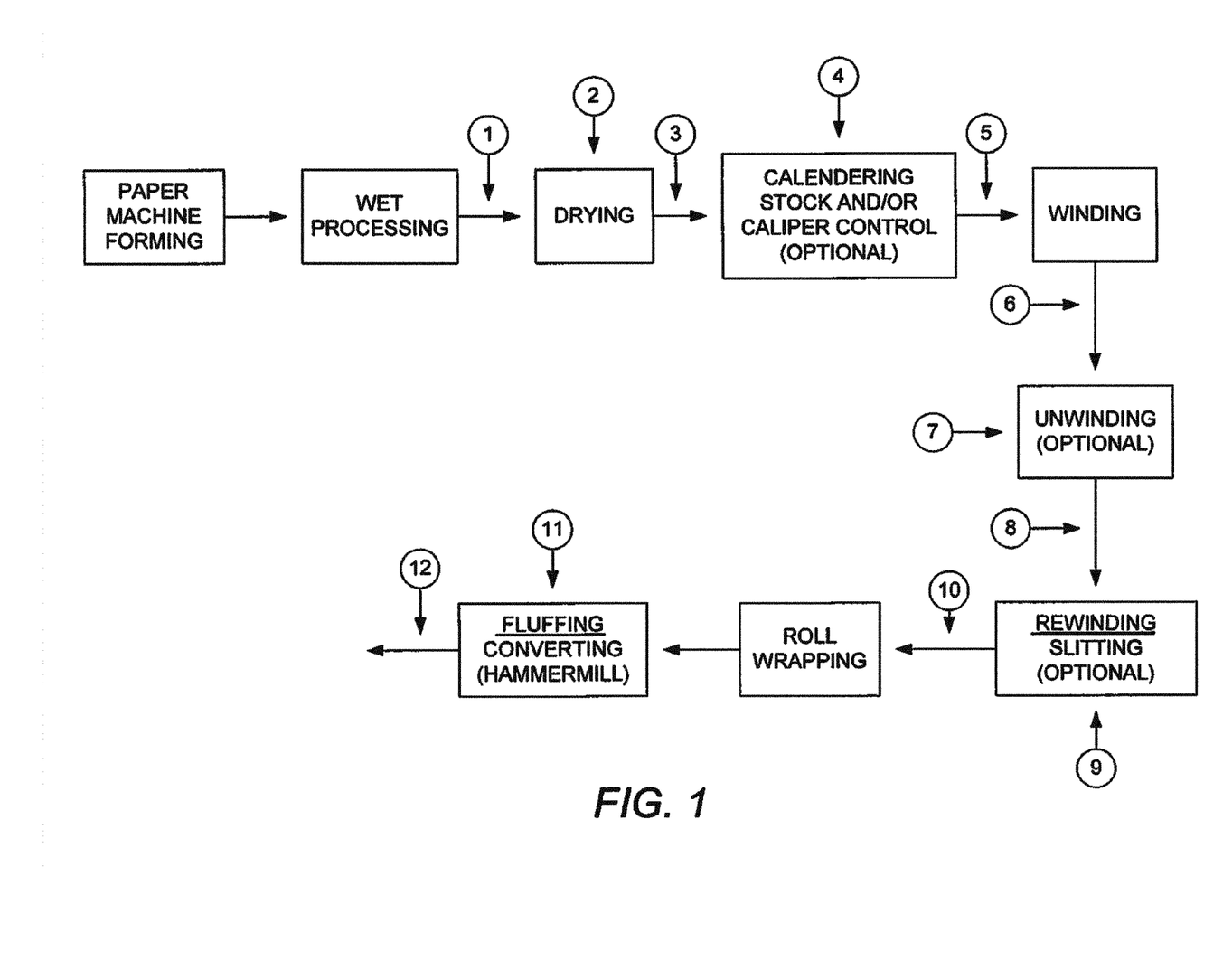
FIG. 1: Pulp making process indicating addition points therein for the compositions of the present invention.

In one embodiment, at least one urease inhibitor is mixed with at least one stabilizer and/or at least one activator; and optionally at least one inert substance to form the composition. Then, this mixture may be contacted with at least one cellulosic fiber. This contacting may occur at any conventional stage during the papermaking or fluff pulp making processes. FIG. 1 depicts these general processes and provides preferable contact points, i.e. 1-6, in which the mixture is contacted with at least one cellulosic fiber. Preferable contact points during this general process are those points depicted as 2-11 in FIG. 1. Most preferable contact points during this general process are those points depicted as 3-11 in FIG. 1. In addition, the contacting may occur by any general method of contacting a mixture with at least one cellulosic fiber such as spraying, curtain coating, coating, roll coating, knife coating, blade coating, size press coating etc. General coating methods may be those mentioned and described in textbooks such as those described in the "Handbook for pulp and paper technologists" by G. A. Smook (1992), Angus Wilde Publications, which is hereby incorporated, in its entirety, by reference. Preferred methods of contacting include coating methods such as liquid spraying, hot-melt spraying, liquid curtain coating and hot-melt curtain coating. More preferred methods of contacting include hydraulic nozzle spraying, atomizing spraying, electrostatic spraying, and hot-melt spraying. The most preferred method of contacting include hydraulic spraying and hot melt spraying.

When the urease inhibitor and the stabilizer are first contacted within one another prior to application to the fiber, the concentrations of the urease inhibitor and the stabilizer may be any concentrations, including from 0.1 to 10 wt %, 0.5 to 7 wt %, 1 to 5 wt %, and 2 to 4 wt %, based upon the total weight of the urease inhibitor and the stabilizer of so long as the concentrations are such that the urease inhibitor has improved stability prior to contacting with the fiber. These concentrations are applicable when the urease inhibitor and the stabilizer are contacted in solid and/or liquid form such that urease inhibitor is dissolved and/or encapsulated by the stabilizer. Again, the concentrations may be much higher when the urease inhibitor and stabilizer are contacted, such as instances in the solid state or in instances forming emulsions, suspensions, colloids, and the like.

In another embodiment, when the composition contains at least one urease inhibitor mixed with at least one stabilizer and/or at least one activator; and optionally at least one inert substance to form the composition; the composition may be contacted with at least one cellulosic fiber when the fiber is a member of a web of cellulosic fibers. In this case, again any of the above-mentioned contacting methods may be employed such that at least one surface of the web is contacted, with the composition. However, the web may have two sides and/or surfaces to it; and, both of these surfaces may be simultaneously or consecutively contacted with the composition by any of the above contacting methods.

When the composition containing at least one urease inhibitor, at least one stabilizer and/or at least one activator, and optionally at least one inert substance is mixed with at least one cellulosic fiber, the weight ratio of the mixture to the cellulosic fiber may be any weight ratio, preferably less than 1:4, more preferably less than 1:9, most preferably less than 1:10. When this mixture is coated onto the cellulosic fiber, any coat weight is acceptable. Preferably, the coat weight is less than 20 wt %, preferably less than 15 wt %, more preferably less than 10 wt %, most preferably less than 5 wt % based upon total weight of the composition including the cellulosic fiber.

After the above-mentioned contacting step, the resulting composition may be optionally dried and/or solidified.

In a particular embodiment, at least one urease inhibitor is contacted with at least one stabilizer optionally in the presence of an inert substance and preferably in substantially no water. The urease inhibitor may or may not be dissolved, but is preferably dissolved, into the at least one stabilizer. This mixture is then contacted with at least one cellulosic material as described above.

In another embodiment, at least one urease inhibitor is contacted with at least one activator in the absence or presence of water. This mixture is then contacted with at least one cellulosic material as described above.

The composition of the present invention is preferably an odor controlling composition. The odor controlling composition may inhibit, prevent, reduce, and/or retard the production of odors in the presence of bodily fluids. Examples of such bodily fluids include urine, urea, blood, menstrual fluid, fecal matter, feces, etc. The composition may control odor caused by the growth of microorganisms in the presence of such bodily fluids. Examples of the microorganisms of interest are those that are able to break down urea into ammonia. In one embodiment, it is most preferable that the composition of the present invention is odor controlling but does not inhibit, prevent, reduce, and/or retard the growth of microorganisms, such as those that are able to breakdown urea into ammonia.

In addition, the composition of the present invention preferably lessens the energy necessary to convert and/or sheer the composition into a fluff pulp product as compared to conventional untreated fluff pulp compositions. In addition, the composition preferably has liquid absorption properties that are not significantly impacted and/or reduced as compared to untreated fluff pulp.

The present invention also relates to an article containing or formed from any of the above-mentioned compositions of the present invention. The article of the present invention is preferably an odor controlling composition. The odor controlling article may inhibit, prevent, reduce, and/or retard the production of odors in the presence of bodily fluids. Examples of such bodily fluids include urine, urea, blood, menstrual fluid, fecal matter, feces, etc. The article may control odor caused by the growth of microorganisms in the presence of such bodily fluids. Examples of the microorganisms of interest are those that are able to break down urea into ammonia. In one embodiment, it is most preferable that the article of the present invention is odor controlling but does not inhibit, prevent, reduce, and/or retard the growth of microorganisms, such as those that are able to breakdown urea into ammonia.

Examples of the article include absorbent articles and fluff pulp. Examples of absorbent articles may include personal hygiene articles and others made of fluff pulp. Examples of personal hygiene articles or products include diapers, fluff pulp, adult incontinence products, feminine hygiene products such as sanitary napkins, etc.

In additional embodiments of the present invention, the compositions and/or articles may be combined with untreated fibers and/or articles that are commonly known. In the case of fibers, treated fibers and compositions containing the same may be contacted, mixed, and/or blended in any way with untreated fibers to produce compositions and/or articles containing a mixture of treated and untreated fibers.

The present invention also relates to a method of reducing the production of ammonia from urea in the presence of at least on microorganism by contacting any one or more of the composition and/or articles mentioned above with urea and at least one microorganism.

The present also relates to a method of reducing the degradation of a urease inhibitor by adding a stabilizer thereto, especially in the presence of a fiber, such that there remains an effective amount of urease inhibitor in the composition and/or article so as to reduce ammonia production when in, the presence of urea and at least one microorganism. The suitable time for such a shelf life may be at least one, week, at least 4 weeks, at least 6 weeks, at least 15 weeks, at least 18 weeks, at least 28 weeks, and at least 52 weeks. The suitable time may include at least 1, 2, 3, 4, 5, 6, 7, 8, 9, 10, 15, 20, 25, 28, 30, 35, 40, 45, 50, 52, 75, 104, 208, and 416 weeks.

As used throughout, ranges are used as a short hand for describing each and every value that is within the range, including all subranges therein.

All of the references, as well as their cited references, cited herein are hereby incorporated by reference with respect to relative portions related to the subject matter of the present invention and all of its embodiments

EXAMPLES

Bacterial Ammonia Test

Test Pad Sample Preparation
1. Place a non-woven carrier on the 50 mm diameter SCAN pad former screen, attach tube, tare, and place on SCAN test piece former.
2. Weigh out 0.60 gm fiberized pulp. Fibers should be "fluffy", well dispersed, and spread evenly in the weighing pan.
3. Sprinkle 0.40 gm SAP evenly over the fiber.
4. Start the vacuum and feed the SAP/fiber into the forming cone through the feed tube, ensuring that both materials are simultaneously introduced.
5. Remove the pad assembly from the former and weigh. Lightly compress the pad and remove the tube.
6. Lift the non-woven carrier with the pad off of the screen.
7. Press to ~3 mm
8. Seal pad wrapped in non-woven in a plastic ziplok bag until testing.
Test Solutions Preparation
Synthetic Urine Make-Up

| | |
|---|---|
| MgSO4, | 0.66 g/750 ml |
| KCl, | 4.47 g/750 ml |
| NaCl, | 7.6 g/750 ml |
| Urea | 18 g/750 ml |
| KH2PO4, | 3.54 g/750 ml |
| Na2HPO4, | 0.745 g/750 ml |

Nutrient Broth

Bacterial Organism and Test Solution Preparation

A broth culture of *Proteus mirabilis* ATCC #7002 is propagated in AOAC Nutrient Broth at 37+/−2° C. for 24 hours. This 24 hour culture contains ~$10^9$ CFU/ml. The culture is further diluted in a synthetic urine/nutrient mix, to give a final bacterial concentration of ~$10^8$ CFU/ml. The synthetic urine has been supplemented with AOAC Nutrient Broth to give a final concentration of 25%. This is the Test Inoculum Solution.

An aliquot of this solution is serially diluted in AOAC phosphate buffer water. Dilutions of $10^{-5}$, $10^{-6}$, $10^{-7}$, and $10^{-8}$ are plated to determine actual number of CPU/ml in the Test Inoculum Solution.

The final Test Inoculum Solution composition is:
75% synthetic urine
25% nutrient broth
$10^7$ CFU/ml *Proteus mirabilis*

Ammonia Measurement

The pad is placed, forming wire side up, into a sterile wide mouth 120 ml septa jar (non-woven carrier removed). The pad is inoculated with 15 ml of the diluted test organism in synthetic urine with 25% AOAC Nutrient Broth, i.e., the Test Inoculum Solution. The jar is sealed and incubated at 35+/−2° C.

At the end of the designated exposure period, the ammonia in the headspace of the sealed jar is measured using the Drager system. The sampling end of the Drager tube is fitted with a needle which is inserted through the septum. A vent needle is inserted to allow withdrawal of the gaseous sample. The opposite end of the measuring tube is attached to the Drager pump. Ammonia is withdrawn according to the manufacturer specifications for the tube and the measurement recorded.

Bleached softwood pulp was made into hand-sheets. The hand-sheets were sprayed with a 400 ppm solution of phenyl phosphorodiamidate (PPDA), to have a PPDA content of 400 ppm on the pulp sheets. The sheets were dried with a lab cylinder drier at 195 F.

The PPDA treated pulp was then shredded by a lab hammermill to convert into fluff fibers. The treated fluff fibers were then mixed with 40% by weight of SAP (superabsorbent polymer) particles, and made into pads for subsequent ammonia generation tests with *Proteus Mirabilis* in synthetic urine. For control, the untreated fluff with 40% SAP was used.

Table 1 shows the test result. It is obvious that the PPDA treated fluff completely prevented any ammonia generation by 8 hrs and 12 hrs tests.

TABLE 1

|  | 8 hrs test | | 12 hrs test | |
| --- | --- | --- | --- | --- |
|  | NH3 concentration | % Reduction of treated fluff against control fluff | NH3 concentration | % Reduction of treated fluff against control fluff |
| Fluff treated with 400 ppm PPDA | 0 ppm | 100% | 0 ppm | 100% |
| Control - Untreated fluff | 650 ppm |  | 1025 ppm |  |

Example 2

Bleached softwood pulp hand sheets were treated with respectively 5 ppm, 50 ppm, 100 ppm and 400 ppm PPDA on the pulp. It was then tested likewise as in Example 1. The result indicated that no ammonia was formed. The % NH3 reduction of treated fluff against untreated fluff, is 100%. No ammonia was generated from any of the treated fluff.

TABLE 2

|  | 8 hrs test % NH3 Reduction of treated fluff against control fluff | 12 hrs test % NH3 Reduction of treated fluff against control fluff |
| --- | --- | --- |
| Fluff treated with 6 ppm PPDA | 99% | 92% |
| Fluff treated with 50 ppm PPDA | 100% | 100% |
| Fluff treated with 100 ppm PPDA | 100% | 100% |
| Fluff treated with 400 ppm PPDA | 100% | 100% |

Bleached softwood pulps that were treated with 400 ppm PPDA was stored on shelf as dry pulp in ambient conditions for 18 weeks and 20 weeks. The aged pulp samples were then fluffed and tested for ammonia generation by bacteria as in Example 1. The result showed that the PPDA inside cellulosic pulp was not stable, and it lost all its effectiveness against ammonia generation in 20 weeks.

TABLE 3

|  | 8 hrs test % NH3 Reduction of treated fluff against control fluff | 12 hrs test % NH3 Reduction of treated fluff against control fluff |
| --- | --- | --- |
| Fluff treated with 400 ppm PPDA - stored for 18 weeks | 12% | 22% |
| Fluff treated with 400 ppm PPDA - stored for 20 weeks | 0% | 3% |

HPLC chromatography test on the 20 week sample showed no PPDA remaining on the pulp.

The 18 week sample had trace amount of PPDA remaining.

It is known that PPDA is not stable in water. But dry PPDA is known to be stable.

For this reason, one would expect PPDA treated fluff pulp (which is dry) would have sufficient stability in storage before use (which would be wetted by urine and other aqueous fluids).

Figure 2:
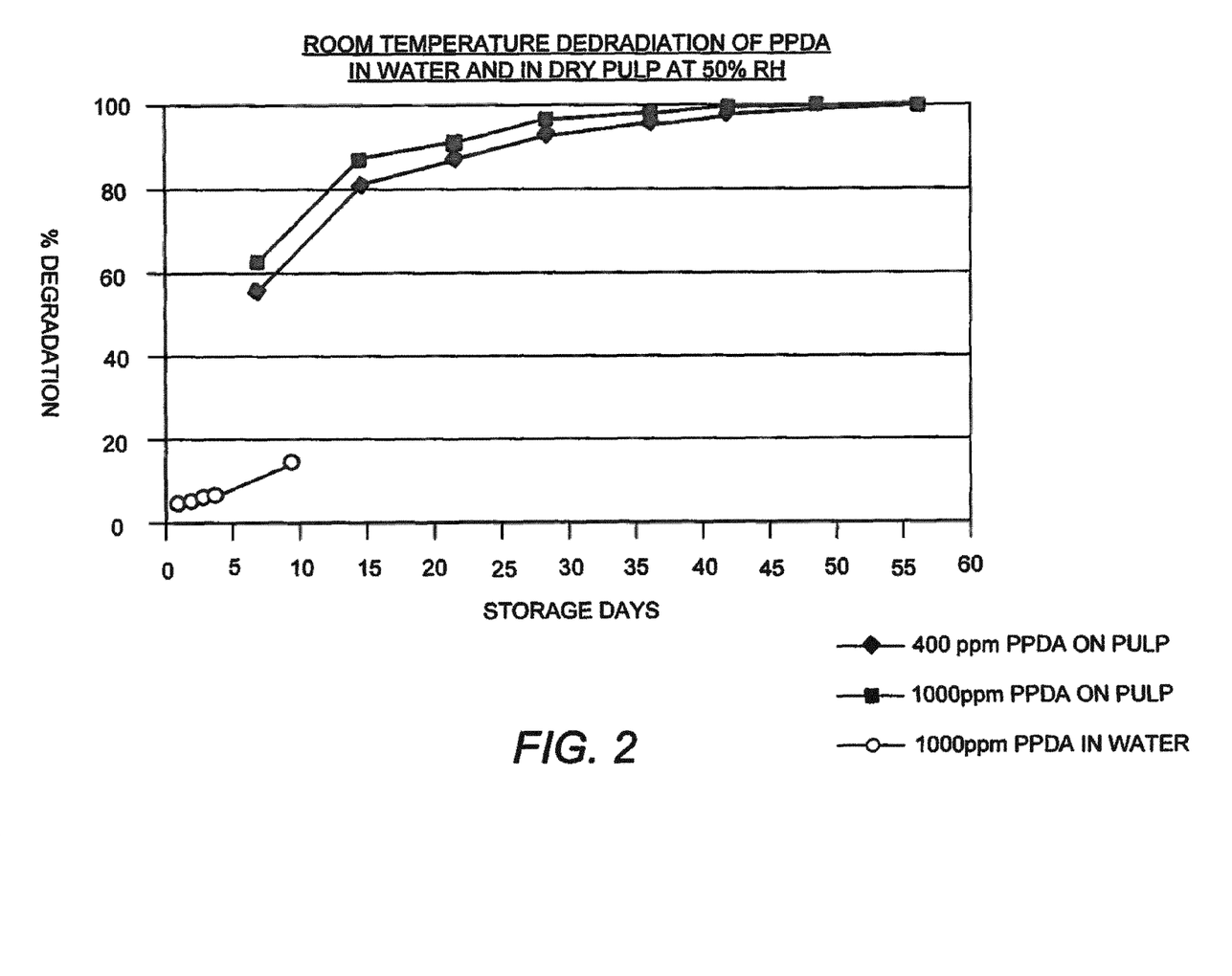
FIG. 2: Results of room temperature degradation studies of PPDA on pulp.
Figure 3:
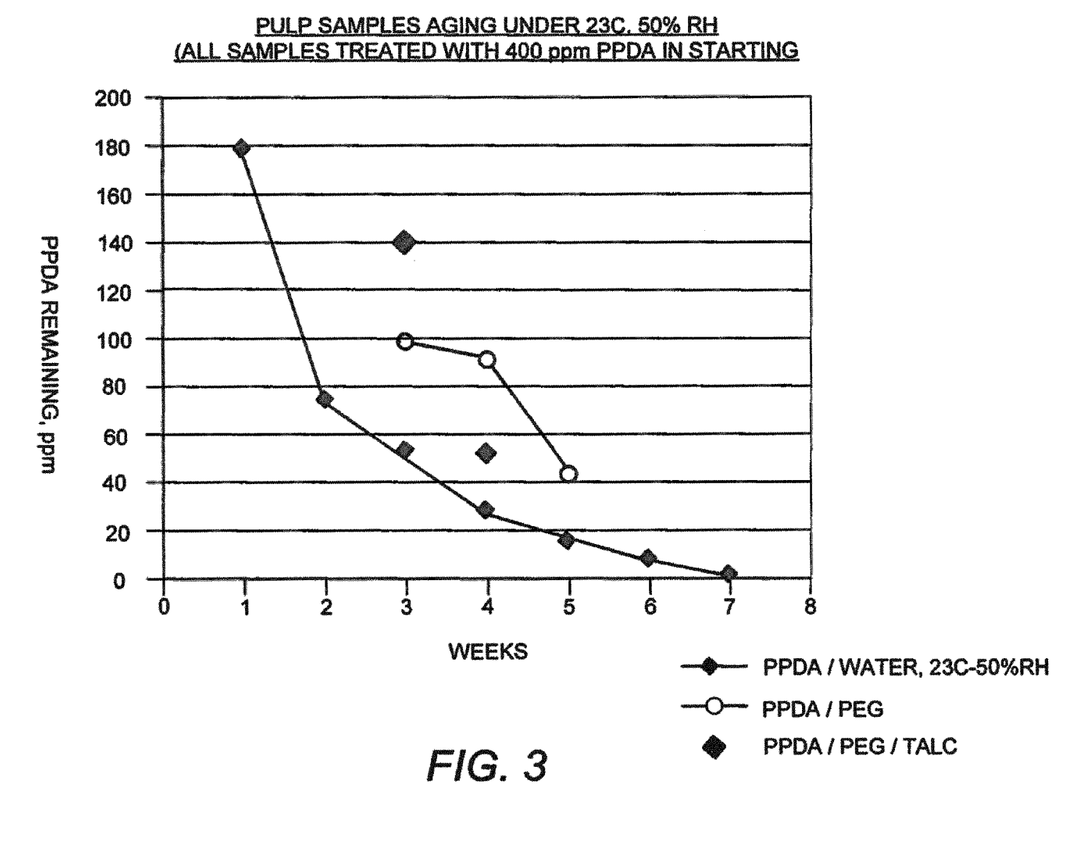
FIG. 3: Results of aging studies of pulp samples.

However, it was quite a surprise that PPDA, when applied on the cellulose pulp, would degrade very fast as shown by the Table 4 below. In fact, it degraded faster in the dry sheet (although only has 50% humidity in the air), than PPDA dissolved in the water. This can be shown in the FIG. 2.

Therefore, there is a critical need of strategies that may delay or reduce the urease inhibitor degradations. This is one embodiment addressed by the present invention.

TABLE 4

| Days in storage | 400 ppm PPDA in Dry Pulp Stored at room temperature and 50% humidity | | 1000 ppm PPDA in Dry Pulp Sored at room temperature and 50% humidity | | 1000 ppm PPDA Dissolved completely in Water at room temperature % Degradation |
| --- | --- | --- | --- | --- | --- |
|  | PPDA concentration remaining in pulp, ppm | % Degradation | PPDA concentration remaining in pulp, ppm | % Degradation |  |
| 1 |  |  |  |  | 5.5% |
| 2 |  |  |  |  | 5.3% |
| 3 |  |  |  |  | 6.3% |
| 4 |  |  |  |  | 6.7% |

TABLE 4-continued

| | 400 ppm PPDA in Dry Pulp Stored at room temperature and 50% humidity | | 1000 ppm PPDA in Dry Pulp Sored at room temperature and 50% humidity | | 1000 ppm PPDA Dissolved |
| --- | --- | --- | --- | --- | --- |
| Days in storage | PPDA concentration remaining in pulp, ppm | % Degradation | PPDA concentration remaining in pulp, ppm | % Degradation | completely in Water at room temperature % Degradation |
| 7 | 179 | 55.3% | 374 | 62.6% | |
| 9 | | | | | 14% |
| 14 | 77 | 80.8% | 133 | 86.7% | |
| 21 | 53 | 86.8% | 95 | 90.5% | |
| 28 | 28 | 93.0% | 38 | 96.2% | |
| 35 | 17 | 95.8% | 16 | 98.4% | |
| 42 | 7 | 98.3% | 7 | 99.3% | |
| 49 | 2 | 99.5% | 2 | 99.8% | |
| 56 | 2 | 99.5% | 3 | 99.7% | |

Example 5

Bleached softwood pulp sheets were treated (sprayed) respectively with: 1) 400 ppm PPDA on pulp from water solution; 2) 400 ppm PPDA on pulp from PEG-200 solution; 3) 400 ppm PPDA on pulp from solution of 90% PEG-200 and 10% Talc powder. All the samples were dried on a dryer can at 195 F. They were then stored under room temperature (23 C.) and 50% humidity chamber. The PPDA content remaining in the dry pulp samples was tested by HPLC.

The results in the figure below showed that PEG, or PEG with talc particles, can all reduce PPDA degradation on dry cellulosic pulps, as compared to the control pulp (treated with PPDA/water and dried).

TABLE 5

| | Aging at 23 C. and 50% RH | | |
| --- | --- | --- | --- |
| Weeks of aging, 23 C., 50% RH | 400 ppm PPDA on pulp from water PPDA remaining | 400 ppm PPDA on pulp from PEG PPDA remaining | 400 ppm PPDA on pulp from PEG/talc PPDA remaining |
| 1 | 179 | | |
| 2 | 77 | | |
| 3 | 53 | 100 | 140 |
| 4 | 28 | 94 | 53 |
| 5 | 17 | 43 | |
| 6 | 7 | | |
| 7 | 2 | | |

Example 6

Figure 4:
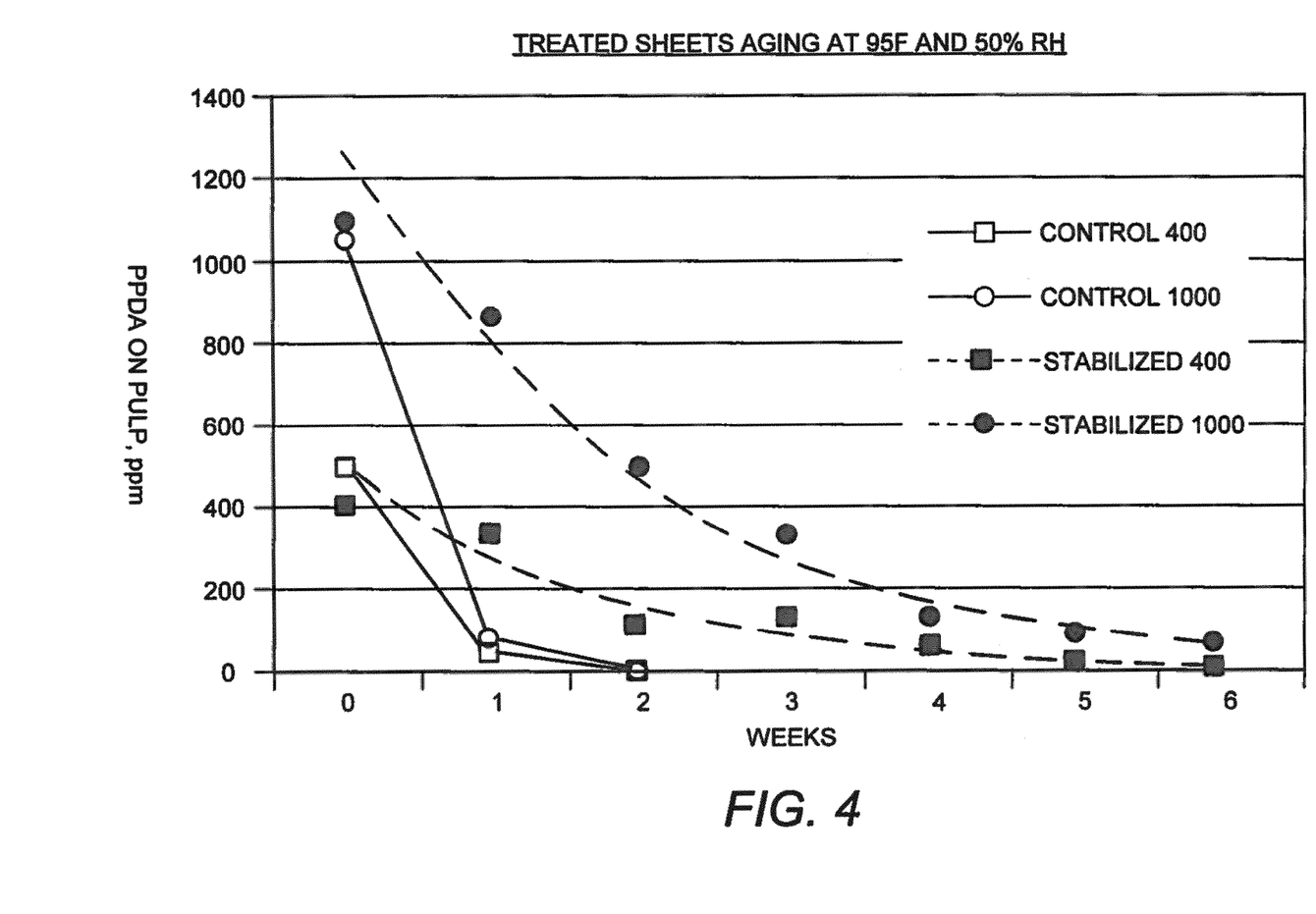
FIG. 4: Results of aging studies of treated sheets.

We have found that PEG and dipropylene glycol (which we had used as the chemical to reduce the PPDA degradation on pulp) had very little degradation of PPDA, which is also corroborated with our previous finding that PEG could be used to substantially reduce the PPDA degradation on the treated fluff pulp. See Table 6 and FIG. 4.

TABLE 6

Making 2% PPDA Solution in Various Types of Glycols

| | NH3 in headspace, ppm Immediately after PPDA dissolution | NH3 in headspace, ppm 4 days in storage |
| --- | --- | --- |
| Propylene glycol | 7.5 | 110 |
| Poly (propylene glycol) | 90 | 380 |
| Dipropylene glycol | 0 | 35 |
| PEG, polyethylene glycol | 0 | 10 |

Example 7

PPDA dissolved in PEG has other advantages over PPDA dissolved in water, in the present application for fluff pulp odor control. It is well known that urease inhibitor PPDA has some unpleasant smell by itself.

In the present invention, we discovered that these smells from PPDA can be suppressed by PEG. In fact, PEG may also be used to suppress and mask other malodors in cellulosic fluff pulps and diapers (including odors from urease inhibitors, and/or odors from bodily fluids in use).

In our example, 0.2% PPDA water solution was compared with 0.2% PPDA in PEG solution. In 40 ml vials, 10 ml of each solution was used (therefore 30 ml headspace). Both GC-MS and human smell were conducted. The results below are self-explanatory.

TABLE 7

| | Phenol in Headspace by GC-MS | Other malodorous compounds detected by GC-MS in the headspace (qualitative) | Smells |
| --- | --- | --- | --- |
| 0.2% PPDA in Water | 1042 ng/ml | Styrene, xytenes, chloro-phenol, nitro-phenol, di-t-butyl benzene, di-butyl quinine, di-t-butyl phenol, and some C4-C9 ketones | Strong bitter, rubbery odors |
| 0.2% PPDA in PEG | 78 ng/ml | Peaks not detected, or suppressed, or masked. | No obvious unpleasant odors |

Example 8

Bleached softwood pulp sheets were treated (sprayed) respectively with:
1) 400 ppm PPDA on pulp from water solution;
2) 400 ppm PPDA on pulp from solution of 90% water and 10% Talc;
3) 400 ppm PPDA on pulp from PEG-200 solution;
4) 400 ppm PPDA on pulp from solution of 90% PEG-200 and 10% Talc powder;
5) 400 ppm PPDA on, pulp from glycerin solution.
All the samples were dried on a dryer can at 195 F.

They were then put into a controlled chamber with temperature of 55 C. and 50% relative humidity. The PPDA content remaining in the dry pulp samples was tested by HPLC.

The results are shown in the table below. Under such conditions of aging in one week, the pulp samples that were treated by PEG, and PEG/Talc still maintain some level of PADA.

TABLE 8

| Treated Pulp Samples, aged 55 C., and 50% RH | PPDA remaining on pulp, after one week |
|---|---|
| 400 ppm PPDA on pulp from water solution | 0 |
| 400 ppm PPDA on pulp from solution of 90% water and 10% Talc | 0 |
| 400 ppm PPDA on pulp from PEG-200 solution | 12 ppm |
| 400 ppm PPDA on pulp from solution of 90% PEG-200 and 10% Talc powder | 7 ppm |
| 400 ppm PPDA on pulp from glycerin solution | 0 |

Example 9

Bleached softwood pulp was treated with 400 ppm NBPT (n-butyl thiophosphoric triamide) on pulp. It was then fluffed, mixed with 40% SAP and tested for ammonia generation by bacteria as in Example 1. In comparison, pulp samples treated with (1) 400 ppm NBPT together with 0.1% 4-hydroxy TEMPO, (2) 400 ppm NBPT with 2.5% hydroxyethyl urea, and (3) pulp treated with 0.1% hydroxyl TEMPO alone were also tested.

It was found that 0.1% TEMPO made the NBPT much more effective in controlling the ammonia generation. TEMPO or TEMPO derivatives were found to be an activator in enhancing the effectiveness of NBPT.

Hydroxyethyl urea was found to be an excellent agent for increasing the solubility of NBPT and PPDA in water (from 0.2%-4.4% concentration, improved to 3%-5% concentrations).

TABLE 9

|  | 8 hrs test % NH3 Reduction of treated fluff against control fluff | 12 hrs test % NH3 Reduction of treated fluff against control fluff |
|---|---|---|
| Fluff treated with 400 ppm NBPT | 82% | 53% |
| Fluff treated with 400 ppm NBPT, together with 2.5% hydroxyl-ethyl urea | 68% | 42% |
| Fluff treated with 400 ppm NBPT, together with 0.1% hydroxyl TEMPO | 94% | 81% |
| Fluff treated with 0.1% TEMPO alone | 29% | 0% |

Example 10

One of many objectives of the present invention, is to control odor (ammonia) formation, without killing bacteria. That is, we would not want to have any biocide, or biocidal effect, while suppressing and controlling odor formation from urine or other bodily fluids. However, killing bacteria, via biocidal effect may occur in other embodiments of the present invention.

Here are some examples below. No significant change of bacteria population was observed, while ammonia formation was suppressed. This is also true with our "activators" (such as hydroxyl TEMPO) that enhance the effectiveness of urease inhibitors (such as NBPT).

TABLE 10

| Fluff Sample Pads | Inoculum of *Proteus mirabilis*, ATCC 7002 CFU/ml | After 8 hrs of incubation (*Proteus mirabilis*) Average Counts per pulp sample pad | After 8 hrs NH3 generated in headspace, ppm |
|---|---|---|---|
| Control (untreated pulp mixed with 40% SAP) | $10^8$ | $1.3 \times 10^{10}$ | 733 |
| Pulp treated with 400 ppm PPDA (mixed with 40% SAP) | $10^8$ | $2.2 \times 10^{10}$ | 0 |
| Pulp treated with 400 ppm PPDA and 0.1% hydroxyl-TEMPO (mixed 40% SAP) | $10^8$ | $1.6 \times 10^{10}$ | 0 |
| Pulp treated with 400 ppm NBPT (mixed 40% SAP) | $10^8$ | not tested | 106 |
| Pulp treated with 400 ppm NBPT and 0.1% hydroxyl-TEMPO (mixed 40% SAP) | $10^8$ | $1.6 \times 10^{10}$ | 39 |

TABLE 10-continued

| Fluff Sample Pads | Inoculum of *Proteus mirabilis*, ATCC 7002 CFU/ml | After 8 hrs of incubation (*Proteus mirabilis*) Average Counts per pulp sample pad | After 8 hrs NH3 generated in headspace, ppm |
|---|---|---|---|
| Special Control (untreated pulp mixed with 40% "Odor-Control-SAP") | $10^8$ | $1.2 \times 10^{10}$ | 326 |

Example 11

Accelerated aging study was done at 35 C. and 50% RH with individual sheets thoroughly exposed to the environment. The control PPDA doses were 400 ppm and 1000 ppm based on the weight of the sheet, applied with water solution and dried. And the stabilized PPDA doses were also at 400 ppm and 1000 ppm on sheet, applied with 2% PPDA solution in PEG-200. The results are shown in the table below, and plotted in FIG. 4.

TABLE 11

Aging at 35 C. and 50% RH

| Weeks of aging at 35 C., 50% RH | Control 400 ppm PPDA Remaining | Control 1000 ppm PPDA remaining | Stabilized 400 ppm PPDA remaining | Stabilized 1000 ppm PPDA remaining |
|---|---|---|---|---|
| 0 | 476 | 1053 | 399 | 1093 |
| 1 | 50 | 74 | 322 | 853 |
| 2 | 0 | 0 | 119 | 488 |
| 3 | | | 123 | 321 |
| 4 | | | 57 | 145 |
| 5 | | | 28 | 95 |
| 6 | | | 11 | 60 |

Figure 5:
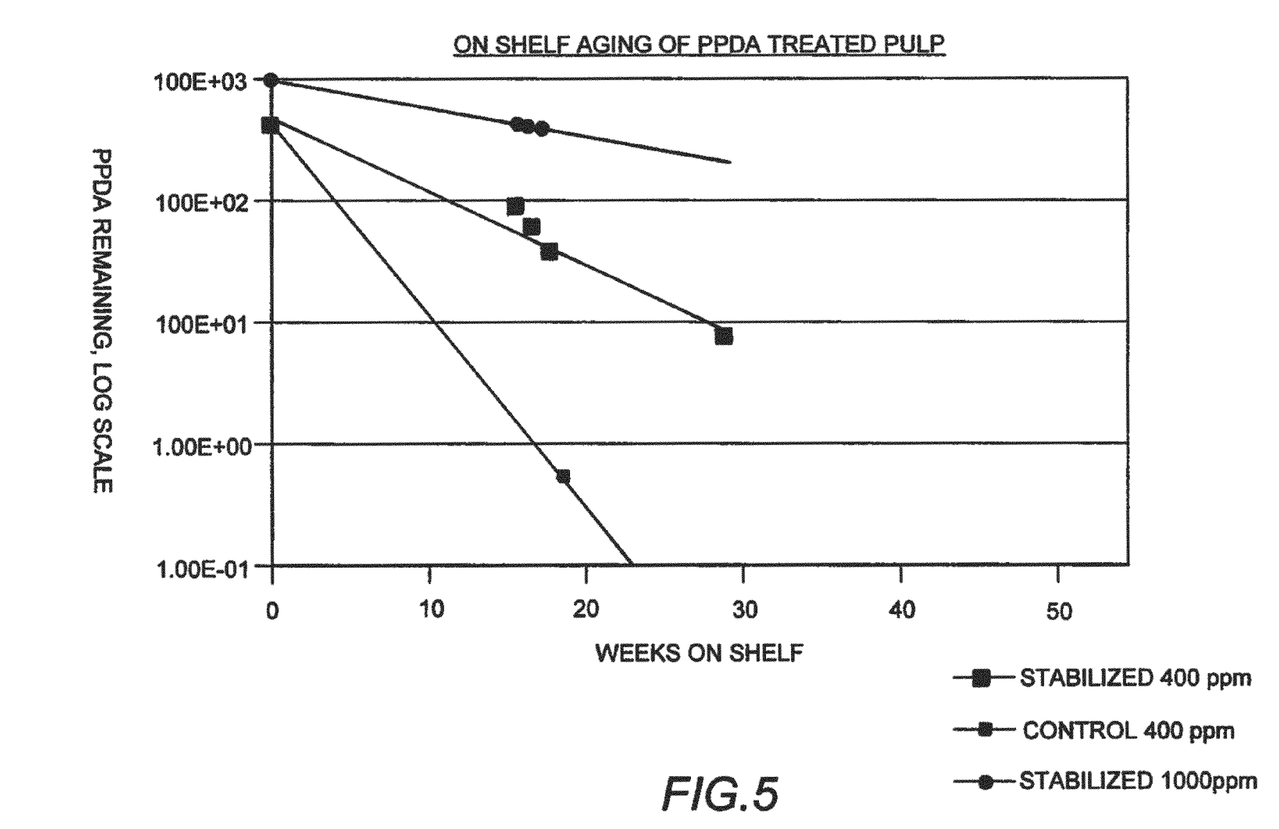
FIG. 5: Results of on shelf aging studies of PPDA treated pulp.

Aging test was also conducted on-shelf in the bag at room conditions. The result was shown in Table 12, and plotted in FIG. 5 in log scale.

TABLE 12

On-Shelf Aging

| Weeks on Shelf | Control 400 ppm (sheets treated with 400 ppm PPDA on pulp from water solution and dried) PPDA on pulp | Stabilized 400 ppm (sheets treated with 400 ppm PPDA on pulp from PEG-200 solution) PPDA on pulp | Stabilized 1000 ppm (sheets treated with 1000 ppm PPDA on pulp from PEG-200 solution) PPDA on pulp |
|---|---|---|---|
| 0 (applied) | 400 | 400 | 1000 |
| 15 | | 87 | 403 |
| 16 | | 57 | 380 |
| 17 | | 33 | 387 |
| 18 | <0.5 | | |
| 28 | | 7 | |

From the results, the control PPDA treated pulp decomposes quickly. On the other hand, with the inventive stabilization composition, the shelf life can be easily extended to beyond half a year (26 weeks). With proper stabilized dose, the shelf life can be expected to extend to 1 year (52 weeks) or beyond as well.

Example 13

As an alternative strategy to Example 10, we may need options to inhibit the growth of various bacterial populations, while preventing ammonia formation through urease inhibition, for multi-odor control. This is especially useful when preventing multiple odors in various bodily, fluids such as menstrual fluid, blood, fecal matter, feces, urea and urine. One strategy is to use anti-microbial polymers together with our stabilized urease inhibitors (with or without commonly used absorbents). In this example, PHMB (polyhexamethylene biguanide) in fluff pulp treatment is used for demonstration. It was found that PHMB treated fluff pulp could inhibit bacterial growth, and it was also found to have some odor control functions by itself.

Other antibacterial polymers include various derivatives of PHMB or functional equivalents thereof (such as PEHMB, PHMG, PEEG, BBIT and boric acid, and those based on quaternary amines, as well as many others such as polynoxylins (a urea-formaldehyde polymer).

TABLE 13

| Fluff Sample Pads | Inoculum of Proteus mirabilis, ATCC 7002 CFU/ml | After 8 hrs of incubation (*Proteus mirabilis*) Average Counts per pulp sample pad | After 8 hrs NH3 generated in headspace, ppm |
|---|---|---|---|
| Control (60% untreated pulp mixed with 40% SAP) | $10^8$ | $1.9 \times 10^{10}$ | 860 |
| Pulp treated with 0.5% PHMB (mixed with 40% SAP) | $10^8$ | $5.6 \times 10^8$ | 600 |
| Special Control (60% untreated pulp mixed with 40% "odor-control-SAP") | $10^8$ | $1.9 \times 10^{10}$ | 342 |

Example 14

There are many commercial products claiming to have odor control functions. Traditionally, odor absorptions or neutralization have been extensively used. Those strategies may only abate the odor molecules within the absorbent capacity. In most cases, the odors are generated over time by urinary tract bacteria, which may quickly go beyond the capacity of the absorbents. Table 14 below shows some of the comparisons of odor control effectiveness among the commercial products, as tested by our method here.

TABLE 14

| Samples | NH3 generated in headspace after 8 hrs of incubation in synthetic urine inoculated with *Proteus mirabilis* |
|---|---|
| Control Lab Pad (60% untreated fluff mixed with 40% SAP) | 700 ppm |

TABLE 14-continued

| Samples | NH3 generated in headspace after 8 hrs of incubation in synthetic urine inoculated with Proteus mirabilis |
|---|---|
| Special Lab Pad Control (untreated fluff mixed with 40% "odor-control SAP") | 400 ppm |
| Commercial Brand A-1 | 480 ppm |
| Commercial Brand A-2 | 363 ppm |
| Commercial Brand B | 700 ppm |
| Commercial Brand C | 750 ppm |
| Commercial Brand D | 760 ppm |
| Commercial Brand E | 780 ppm |
| Commercial Brand F | 920 ppm |
| Control Lab Pad (60% untreated fluff mixed with 40% SAP) | 900 ppm |
| Fluff treated with 400 ppm PPDA (stabilized with PEG-200), after aged 14 weeks, (mixed with 40% SAP) | <6 ppm |

It is shown that the inventive composition and article of the present invention containing stabilized urease inhibitor is substantially more effective than any commercial products tested so far. Brand A-1 and Band A-2, which are relatively more effective than other commercial products, are probably based on "odor-control SAP (superabsorbent polymer)" technologies.

Example 15

All the activators disclosed (including by not limited to tempos, laccase mediators, oxidative enzymes, etc) may have urease inhibition by themselves, as shown by some of our examples. These activators may also be compatible with our stabilized urease inhibitors.

For instance, violuric acid when dissolved in water displays strong pink colors. The pink color can "dye" the pulp as well, especially when metal ions are present. The well-known discoloration by violuric acid, however, can be alleviated by dissolving violuric acid in PEG-200 (non-aqueous) which displays a dim blueish color. The violuric acid in PEG solution is compatible with stabilized urease inhibitors such as PPDA and others.

In general, all the activators can be compatible with the urease inhibitors stabilized by PEG.

Example 16

Solid PEG particles (CartaCoat GP from Clariant) were mixed with 1% by weight of PPDA powders. The solid mixtures were then heated at 80 C. until all the PEG melted. After stirring, the molten mixture was then let to cool down into solids.
The solid blocks stabilized the PPDA, and the blocks can also be "rubbed" against the moving fluff web as one of the coating application of the stabilized urease inhibitors.
The molten solid may also be made into particles (ground powders, granules, etc) and/or mixed with SAP particles. Such, particles alone or in, combination with SAP particles may be added to fibers prior to, during, or after during any converting operation (such as hammermills).
This applies to all stabilized urease inhibitors and activators (and/or other inert particles/absorbents).

Example 17

Figure 6:
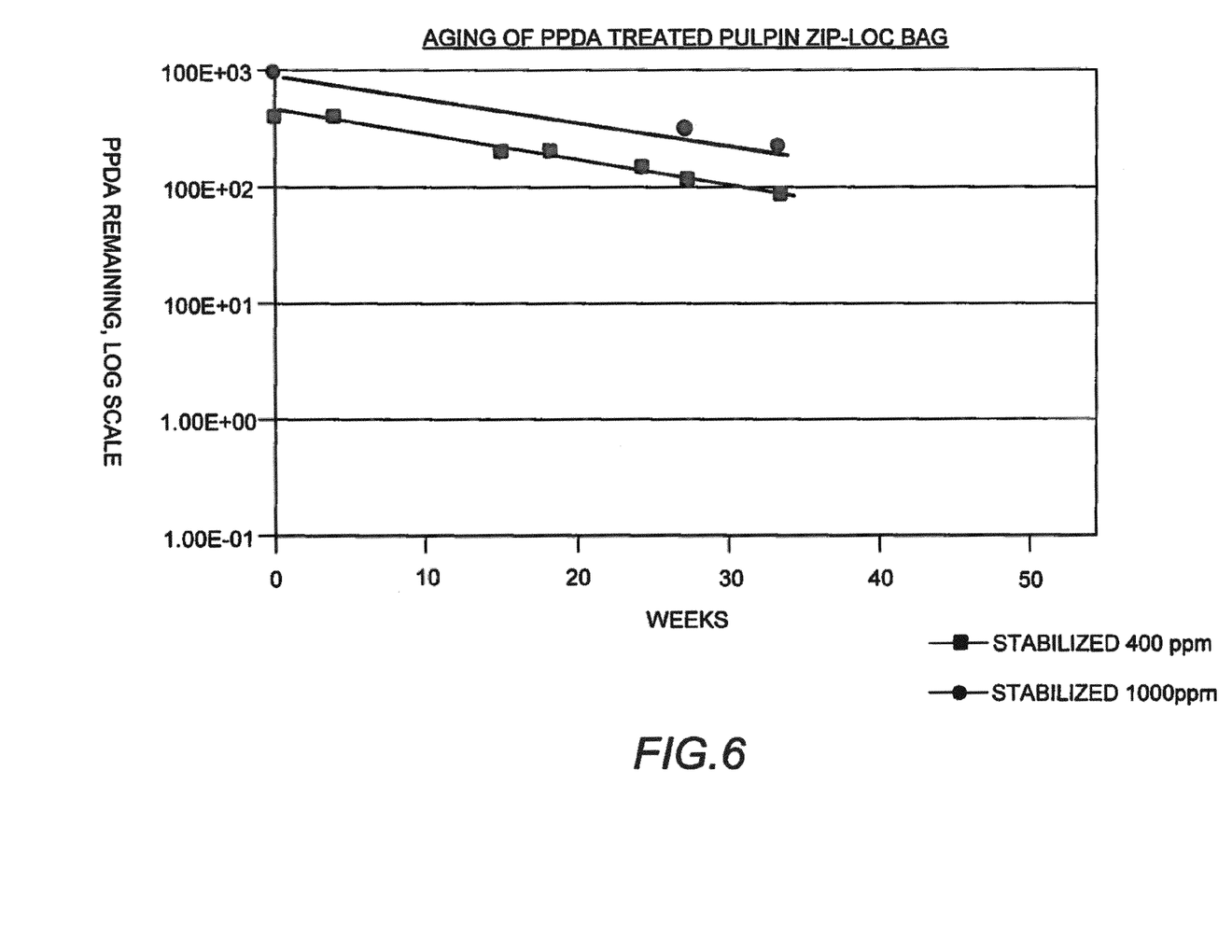
FIG. 6: Results of aging studies of pulp samples in zip lock bag.

Storage of treated pulp samples, as prepared in Example 12, inside Zip-Loc plastic bags have slightly improved stability. The results are shown in Table 15, and FIG. 6 below.

TABLE 15

| | Aging in Zip-Loc Bag on Shelf | |
|---|---|---|
| Weeks in Zip-Loc Bag | Stabilized 400 ppm (sheets treated with 400 ppm PPDA on pulp from PEG-200 solution) PPDA on Pulp | Stabilized 1000 ppm (sheets treated with 1000 ppm PPDA on pulp from PEG-200 solution) PPDA on Pulp |
| 0 (applied) | 400 | 1000 |
| 4 | 426 | |
| 15 | 211 | |
| 18 | 209 | |
| 24 | 154 | |
| 27 | 117 | 317 |
| 33 | 88 | 221 |

Numerous modifications and variations on the present invention are possible in light of the above teachings. It is, therefore, to be understood that within the scope of the accompanying claims the invention may be practiced otherwise than as specifically described herein.

What is claimed is:

1. A composition, comprising
   at least one cellulosic fiber;
   phenyl phosphorodiamidate (PPDA) as urease inhibitor; and
   0.1 to 20 wt %, based upon the total weight of the composition, of a stabilizer for the PPDA selected from the group consisting of polyethylene glycol, dipropylene glycol, and a mixture thereof, wherein the polyethylene glycol comprises PEG-200.

2. The composition according to claim 1, wherein the composition comprises substantially no water.

3. The composition according to claim 1, further comprising an inert substance.

4. The composition according to claim 1, further comprising at least one member selected from the group consisting of a n-alkyl phosphoric triamide, n-alkyl thiophosphoric triamide, and a mixture thereof.

5. The composition according to claim 1, further comprising n-butyl thiophosphoric triamide (NBPT).

6. The composition according to claim 1, comprising from 0.5 ppm to 10 wt % of the PPDA based upon the total weight of the composition.

7. The composition according to claim 1, wherein the stabilizer is PEG-200.

8. The composition according to claim 1, wherein the stabilizer is dipropylene glycol.

9. The composition according claim 1, further comprising at least one inert material selected from the group consisting of water absorbing compounds and water barrier forming compounds.

10. The composition according to claim 1, further comprising at least one superabsorbent particle.

11. The composition according to claim 1, further comprising talc.

12. The composition according to claim 1, comprising from 0.1 to 10 wt % of at least one inert material based upon the total weight of the composition.

13. A method of making the composition according to claim 1, comprising consecutively or simultaneously contacting the at least one cellulosic fiber with the PPDA and the stabilizer.

14. The method according to claim 13, further comprising pre-mixing the PPDA and the stabilizer to form a precursor composition; and contacting the precursor composition with the at least one cellulosic fiber.

15. The method according to claim 13, further comprising drying the composition.

16. The method according to 13, wherein said contacting is performed by simultaneously or consecutively spraying the PPDA and the stabilizer onto at least one surface of a web of cellulosic fibers.

17. An article, comprising the composition according to claim 1.

18. The article according to claim 17, wherein the article is at least one member selected from the group consisting of an absorbent article and a personal hygiene article.

19. The article according to claim 17, wherein the article is selected from the group consisting of a diaper, a feminine hygiene article, and an adult incontinency product.

20. The article according to claim 17, further comprising at least one super absorbent particle.

21. A method of making the article according to claim 20, comprising simultaneously or consecutively contacting the at least one super absorbent particle with the composition.

22. A method of inhibiting the production of ammonia from urea in the presence of at least one microorganism, comprising contacting the article according to claim 17 with urea and at least one microorganism.

23. The method according to claim 22, wherein the article does not substantially inhibit the growth of the at least one microorganism.

24. The composition according to claim 1, wherein the stabilizer has a $T_m$ that ranges from room temperature to 120° C.

25. The composition according to claim 24, wherein the stabilizer forms a matrix in which the PPDA, the at least one cellulosic fiber, and at least one super absorbent particle reside.

26. The composition according to claim 1, wherein the stabilizer is a mixture of PEG-200 and dipropylene glycol.

27. The composition according to claim 1, comprising from 1 ppm to 10 wt % of the PPDA based upon the total weight of the composition.

28. The composition according to claim 1, comprising from 5 ppm to 10 wt % of the PPDA based upon the total weight of the composition.

29. The composition according to claim 1, comprising from 50 ppm to 10 wt % of the PPDA based upon the total weight of the composition.

30. The composition according to claim 1, comprising from 100 ppm to 10 wt % of the PPDA based upon the total weight of the composition.

31. The composition according to claim 1, comprising from 400 ppm to 10 wt % of the PPDA based upon the total weight of the composition.

* * * * *